United States Patent [19]
Onda et al.

[11] Patent Number: 5,376,535
[45] Date of Patent: Dec. 27, 1994

[54] METHOD FOR PRODUCING 3'-PHOSPHOADENOSINE 5'-PHOSPHOSULFATE

[75] Inventors: Masaaki Onda; Hiroshi Ibuki; Hiroshi Nakajima, all of Kyoto, Japan

[73] Assignee: Unitika Ltd., Hyogo, Japan

[21] Appl. No.: 974,216

[22] Filed: Nov. 10, 1992

[30] Foreign Application Priority Data

Nov. 14, 1991 [JP] Japan .................................. 3-326951

[51] Int. Cl.$^5$ ......................... C12P 19/30; C12P 19/32
[52] U.S. Cl. .......................................... 435/92; 435/89
[58] Field of Search ..................................... 435/89, 92

[56] References Cited

U.S. PATENT DOCUMENTS 4,164,444 8/1979 Whitesides et al. ................... 438/92
4,266,048 5/1981 Horwitz et al. ........................ 435/89

FOREIGN PATENT DOCUMENTS 41-17632 10/1966 Japan .

OTHER PUBLICATIONS

R. Cherniak et al., "Synthesis of Adenylyl Sulfate and Adenylyl Sulfate 3'-Phosphate", The Journal of Biological Chemistry, vol. 239, No. 9, Sep. 1964, pp. 2986–2990.
"Methods in Enzymology", Edited by S. P. Colowick, N. O. Kaplan, P. W. Robbins, vol. 5, Academic Press, Inc., New York and London, (1962) p. 964.
S. S. Singer, "Enzymatic Sulfation of Steroids. VI. A Simple, Rapid Method for Routine Enzymatic Preparation of 3'–Phosphoadenosine–5'–Phosphosulfate", Anal. Biochem., vol. 96, (1979) pp. 34–38.

*Primary Examiner*—Herbert J. Lilling
*Attorney, Agent, or Firm*—Sughrue, Mion, Zinn, Macpeak & Seas

[57] ABSTRACT

A method for producing 3'-phosphoadenosine 5'-phosphosulfate, which comprises (1) reacting adenosine 5'-triphosphate with a sulfate donor in the presence of heat-stable adenosine 5'-triphosphate sulfurylase to produce adenosine 5'-phosphosulfate, and (2) reacting said adenosine 5'-phosphosulfate with adenosine 5'-triphosphate in the presence of heat-stable adenosine 5'-phosphosulfate kinase; and another method for producing 3'-phosphoadenosine 5'-phosphosulfate which comprises (1) reacting adenosine 5'-triphosphate with a sulfate donor in the presence of adenosine 5'-triphosphate sulfurylase to produce adenosine 5'-phosphosulfate, (2) reacting said adenosine 5'-phosphosulfate with adenosine 5'-triphosphate in the presence of adenosine 5'-phosphosulfate kinase to produce 3'-phosphoadenosine 5'-phosphosulfate and adenosine 5'-diphosphate, and (3) converting said adenosine 5'-diphosphate into adenosine 5'-triphosphate in the presence of a phosphate donor and an enzyme capable of converting adenosine 5'-diphosphate into adenosine 5'-triphosphate are disclosed.

12 Claims, No Drawings

METHOD FOR PRODUCING 3'-PHOSPHOADENOSINE 5'-PHOSPHOSULFATE

FIELD OF THE INVENTION

This invention relates to a method for producing 3'-phosphoadenosine 5'-phosphosulfate (referred to simply as PAPS hereinafter).

BACKGROUND OF THE INVENTION

It is said that PAPS of a structure represented by the formula:

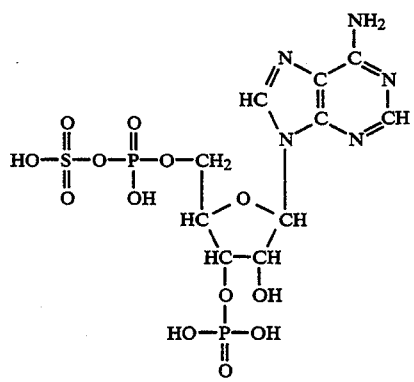

serves as the sulfate donor for all sulfation reactions known to occur in the cells of higher animals. In higher animals, sulfation reactions are involved in a variety of biochemical/physiological processes which include the detoxication of xenobiotics, the metabolism of catecholamine-type of neurotransmitters, the biosynthesis of sulfated proteins and sulfated proteoglycans. There have also been reports showing a correlation between the sulfation level of biomolecules and the cellular oncogenic transformation. Namely, PAPS plays very important roles in vivo and, therefore, it is highly useful in the fields of, for example, drugs. However, none of the known methods for producing this compound is applicable on an industrial scale or has been put into practical use. As an example of a method for chemically synthesizing PAPS, the one reported by Robert et al. may be cited [refer to R. Cherniak et al., J.B.C., 239, 2986 (1964)]. As an example of a fermentation method for producing PAPS, a method with the use of a bacterium belonging to the genus Streptomyces is reported [refer to JP-B-41-17632; the term "JP-B" as used herein means an "examined Japanese patent publication"]. Examples of known methods for enzymatically producing PAPS include those wherein PAPS is produced from adenosine 5'-triphosphate (hereinafter referred to simply as ATP) by a two-stage reaction with the use of adenosine 5'-triphosphate sulfurylase (hereinafter referred to simply as ATP sulfurylase) and adenosine 5'-phosphosulfate kinase (hereinafter referred to simply as APS kinase) extracted from baker's yeast [refer to "Methods in Enzymology", ed. by S. P. Colowick, N. O. Kaplan, P. W. Robbins., 5, 964, Academic Press Inc., New York and London, 1962, ] or rat liver [refer to S. S. Singer, Anal. Biochem., 96, 34 (1979)].

However, each of these methods makes it possible to produce only several to several tens of milligrams of PAPS and, therefore, is of no practical use from an industrial viewpoint. That is to say, the chemical methods cannot be scaled up since reagents which are difficult to handle and a complicated reaction are needed therein. In the fermentation methods, only a trace amount of PAPS is accumulated and it is very difficult to separate this product from cells or media. By the enzymatic synthesis of PAPS, one molecule of PAPS is formed from two molecules of ATP and one molecule of adenosine 5'-diphosphate (hereinafter referred to simply as ADP) is simultaneously formed as a side product, as the following (chemical equation 4) shows. Therefore, the enzymatic methods are disadvantageous in that the yield of PAPS, based on the ATP, is 50% at the highest.

(chemical equation 1)
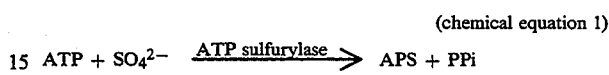

(chemical equation 2)

(chemical equation 3)
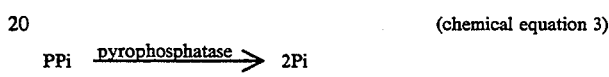

(chemical equation 4)

In the above chemical equations, PPi is pyrophosphoric acid and Pi is phosphoric acid. As described above, it is very difficult to produce PAPS on an industrial scale.

It is an object of the present invention to provide a method for producing PAPS from ATP by a two-stage reaction with the use of at least two enzymes, i.e., ATP sulfurylase and APS kinase, whereby PAPS can be produced in a large amount and easily isolated.

SUMMARY OF THE INVENTION

In order to achieve the above-mentioned object, the present inventors have conducted extensive investigations. As a result, they have found out that when heat-stable enzymes are used as the two enzymes, namely, ATP sulfurylase and APS kinase, to be used in the enzymatic synthesis of PAPS, the yield of the product is surprisingly and remarkably increased, the PAPS can be easily isolated and purified, and further, the substrate ATP can be used at a high concentration, thus being advantageous for the industrial production of PAPS. Thus the first embodiment of the present invention has been completed. The inventors have further found out that when an enzyme capable of converting ADP into ATP is present together with the above-mentioned two enzymes, namely, ATP sulfurylase and APS kinase in the enzymatic synthesis of PAPS, the yield of PAPS based on ATP can be remarkably increased. Thus the second embodiment of the present invention has been completed.

The present invention relates to the method for producing 3'-phosphoadenosine 5'-phosphosulfate which comprises (1) reacting adenosine 5'-triphosphate with a sulfate donor in the presence of heat-stable adenosine 5'-triphosphate sulfurylase to produce adenosine 5'-phosphosulfate, and (2) reacting said adenosine 5'-phosphosulfate with adenosine 5'-triphosphate in the presence of heat-stable adenosine 5'-phosphosulfate kinase and to the method for producing 3'-phosphoadenosine 5'-phosphosulfate which comprises (1) reacting adenosine 5'-triphosphate with a sulfate donor in the presence of adenosine 5'-triphosphate sulfurylase to produce adenosine 5'-phosphosulfate, (2) reacting said adenosine 5'-phosphosulfate with adenosine 5'-triphosphate in the presence of adenosine 5'-phosphosulfate kinase to produce 3'-phosphoadenosine 5'-phosphosulfate and adenosine 5'-diphosphate, and (3) converting said adenosine 5'-diphosphate into adenosine 5'-triphosphate in the presence of a phosphate donor and an enzyme capable of converting adenosine 5'-diphosphate into adenosine 5'-triphosphate.

Accordingly, the gist of the first embodiment of the present invention resides in a method for producing PAPS characterized in that when PAPS is produced from ATP by a two-stage reaction with the use of ATP sulfurylase and APS kinase as catalysts, the two enzymes to be used as catalysts are heat-stable ones. On the other hand, the gist of the second embodiment of the present invention resides in a method for producing PAPS characterized in that when PAPS is produced from ATP by the two-stage reaction with the use of ATP sulfurylase and APS kinase as catalysts, an enzyme capable of converting ADP into ATP is also present.

DETAILED DESCRIPTION OF THE INVENTION

The two embodiments of the present invention will be described in greater detail.

As described above, the enzymatic reaction relating to the method for producing PAPS according to the first and second embodiments comprises converting ATP into a sulfate, i.e., adenosine 5'-phosphosulfate (hereinafter referred to as APS), under the catalytic action of non-heat stable or heat-stable (depending upon the embodiment) ATP sulfurylase (chemical equation 1), and phosphorylating the 3'-hydroxyl group of the APS thus formed using ATP as a phosphate donor under the catalytic action of non-heat stable or heat-stable (depending upon the embodiment) APS kinase (chemical equation 2). Further, in the second embodiment, the reactions are conducted in the presence of an enzyme capable of converting ADP formed in chemical equation 2 into ATP with the use of acetyl phosphate (hereinafter referred to simply as AcOP) as a phosphate donor.

It is usually preferable that an enzyme capable of hydrolyzing pyrophosphoric acid into phosphoric acid, namely, pyrophosphatase (hereinafter referred to simply as PPase) is present so as to further shift the equilibrium to the formation of PAPS, as chemical equation 3 shows.

In the first embodiment of the present invention, the ATP sulfurylase and the APS kinase should be heat-stable ones. Although the origins of these enzymes are not particularly restricted, those obtained from thermophilic bacteria may be cited as examples thereof. The heat-stable enzyme of the present invention has an optimal temperature for its activity of about 40° C. or higher, preferably, from about 40° C. to about 100° C. Examples of thermophilic bacteria useful for obtaining the heat-stable enzymes include those belonging to the genus Bacillus such as *Bacillus stearothermophilus, Bacillus brevis, Bacillus coagulans, Bacillus thermoproteolytics* and *Bacillus acidocaldarius*, those belonging to the genera Clostridium, Thermoactinomyces, Achromobacter, Streptomyces and Micropolyspora, those belonging to the genus Thermus such as *Thermus aquaticus, Thermus thermophilus* and *Thermus flavus* and those belonging to the genera Thermomicrobium and Cardelia. Examples of particular strains include *Bacillus stearothermophilus* (NCA 1503; ATCC 29609), *Thermus flavus* (ATCC 33923), and *Bacillus coagulans* (ATCC 7050).

In addition, bacteria which grow at room temperature and contain genes of heat-stable ATP sulfurylase and heat-stable APS kinase to produce such enzymes are also involved. The ATP sulfurylase and the APS kinase to be used in the second embodiment of the present invention may be any ATP sulfurylase and APS kinase, so long as they can synthesize PAPS when used together. Particular examples thereof include enzymes originated from *Escherichia coli*, those originating from yeasts and those originating from thermophilic bacteria belonging to the genus, for example, Bacillus or Thermus. It is particularly preferable to use enzymes originating from thermophilic bacteria. As examples of these thermophilic bacteria, the above-mentioned ones may be cited.

As the enzyme capable of converting ADP into ATP to be used in the second embodiment of the present invention, a number of enzymes including acetate kinase, carbamate kinase, creatine kinase, 3-phosphoglycerate kinase, pyruvate kinase and polyphosphate kinase may be used. It is most advantageous to select acetate kinase, from among these enzymes, from the view, point of availability.

Regarding the origin of the enzyme for converting ADP into ATP, enzymes originating from *Escherichia coli*, those originating from yeasts and those originating from thermophilic bacteria belonging to the genus, for example, Bacillus or Thermus may be cited. It is particularly preferable to use enzymes originating from thermophilic bacteria. Examples thereof include those as cited above. *Escherichia coli*, yeasts and thermophilic bacteria belonging to the genus, for example, Bacillus or Thermus may be cultured by conventional methods.

The enriched medium to be used for incubating a bacterium or an yeast in the present invention may contain carbon sources, for example, sugars such as glucose, sucrose, fructose, starch hydrolysates, molasses and sulfite waste liquor, organic acids such as acetic acid and lactic acid, and alcohols, fats and oils, fatty acids and glycerols which can be metabolized by the bacterium employed. It may further contain nitrogen sources, for example, organic and inorganic substances such as ammonium sulfate, ammonium phosphate, ammonia, amino acids, peptone, meat extract and yeast extract and, furthermore, inorganic salts such as potassium, sodium, phosphoric acid, zinc, iron, magnesium, manganese, copper, calcium and cobalt salts. Furthermore, it may contain trace metals, corn steep liquor, vitamins and nucleic acids, if necessary. Thus enriched media commonly employed for incubating bacteria may be used.

The bacterium may be incubated in such a medium at a temperature of from 20° to 80° C., preferably from 40° to 70° C. and most preferably at about 60° C. for 2 to 6 hours, under aerobic conditions. The yeast may be incubated in such a medium at a temperature of from 25° C. to 35° C., preferably from 27° C. to 33° C.

In order to obtain the above-mentioned three enzymes from the bacteria or the yeast, the cells are first collected from the culture medium =and then disrupted by, for example, treating with a homogenizer, a blender, a dynomill or a French press, ultrasonicating, freezing and thawing or treating with lysozyme.

Next, a cationic polymer coagulant is added to the above-mentioned disrupted cell suspension (cell extract) to thereby precipitate the disrupted cell fragments and nucleic acids.

Examples of the polymer coagulant usable in the present invention include polyaminoalkyl methacrylates, polyaminoalkyl methacrylate/acrylamide copolymers, Mannich-modified polyacrylamides, polydimethyldiallylammonium salts, polyvinylimidazolines, polyacrylamides and amine polycondensates.

The amount of the polymer coagulant to be added may preferably range from 1 to 40 parts by weight per 100 parts by weight of the disrupted microbial cells on a dry basis, though it may vary depending on the polymer coagulant. This cationic polymer coagulant is previously dissolved in water and then added to the disrupted cell suspension, followed by stirring for 10 minutes to 24 hours. If necessary, the pH value may be optionally controlled by adding from 10 to 200 mM of a buffer solution. Further, from 1 to 50 parts by weight, per 100 parts by weight of the disrupted cell suspension, of glucose may be added in order to stabilize the protein.

Subsequently, the disrupted cell fragments and nucleic acid thus precipitated are separated by, for example, allowing the mixture to 2stand, centrifuging or filtering.

Thus a crude enzyme preparation can be obtained. A further purified enzyme preparation may be obtained by using various chromatographic techniques, for example, gel filtration chromatography, hydrophobic chromatography or ion exchange chromatography as is well known in the art.

The method for producing PAPS according to the first embodiment of the present invention may be performed by, for example, feeding a buffer solution, ATP, a sulfate donor capable of producing sulfate ion ($SO_4^{2-}$), magnesium ion ($Mg^{2+}$), heat-stable ATP sulfurylase and heat-stable APS kinase in a single reactor together and reacting with each other. Herein, magnesium ion activates ATP and it is preferable to be present so as to promote the reaction. Examples of the sulfate donor include magnesium sulfate, sodium sulfate, potassium sulfate, lithium sulfate, and beryllium sulfate. Further, PPase may coexist, if necessary or if desired.

In the method for producing PAPS according to the first embodiment of the present invention, it is still preferable that an enzyme capable of converting ADP into ATP and a phosphate donor are further present together and reacted.

The method for producing PAPS according to the second embodiment of the present invention may be performed by, for example, feeding a buffer solution, ATP, a sulfate donor capable of producing sulfate ion ($SO_4^{2-}$), magnesium ion ($Mg^{2+}$), ATP sulfurylase, APS kinase, an enzyme capable of converting ADP into ATP and a phosphate donor in a single reactor together and reacting with each other. Further, PPase may be present, if necessary or if desired. The enzyme capable of converting ADP into ATP is preferably a heat-stable one.

Any reactor may be used in the above-mentioned methods, so long as it allows the smooth progress of the reaction. The size and the type of the reactor may be determined depending on, for example, the amount of each enzyme, the substrate concentration, the pH value, the feeding rates and the reaction temperature. Regarding the type of the reactor, either a membrane reactor or a column one may be used. In particular, a membrane reactor may be effectively used in the present invention, since the reaction product has a low molecular weight. In this case, the enzymes, which are high molecular weight substances, may be used while remaining in the reactor. In the case of a column reactor, the enzymes to be used may be formulated into so-called immobilized enzymes by binding to, including in or adsorbing on a suitable carrier (for example, polysaccharide derivatives such as cellulose, dextran or agarose; vinyl polymer derivatives such as polystyrene, ethylene/maleic acid copolymer or cross-linked polyacrylamide; poly(amino acid) or polyamide derivatives such as L-alanine-L-glutamic acid copolymer or polyaspartic acid; or inorganic substances such as glass, alumina or hydroxyapatite) and then packed into the column.

The above-mentioned reactors are illustrated on the assumption of continuous operation. Alternately, other reactors may be used based on the above consideration. It is also possible that a batch reaction can be carried out with the use of a batch type reactor.

Now, reaction conditions for the production of PAPS will be described. The pH value at the reaction may vary depending on the enzymes. In general, the reaction may be performed under almost neutral condition, namely, at pH 5 to 11, preferably at pH 6 to 9. The pH value may be controlled with a buffer solution. This buffer solution may be selected from among commonly employed ones suitable for the above-mentioned pH value.

The reaction temperature is not particularly restricted, so long as the enzymes are not inactivated and the reaction can smoothly proceed. A reaction temperature of from 20° to 70° C., in particular, from 25° to 45° C., is preferable.

The concentration Of ATP is not particularly restricted. A concentration of 200 mM or lower, more particularly, 100 mM or lower is preferable. Further, the concentration of ATP is preferably not less than 0.01 mM The sulfate and magnesium ions may be added in any form. It is preferable that the sulfate ion concentration is approximately twice as high as the ATP concentration while the magnesium concentration ranges from 1 mM (equivalent) to 100 mM (equivalent).

The ATP sulfurylase may be used in an amount of from 5 mU/ml to 200 mU/ml. The APS kinase may be preferably used in an amount of twice (by unit) as much as the ATP sulfurylase. The PPase may be preferably used in an amount of from 5 U/ml to 100 U/ml. The acetate kinase, or other enzyme capable of converting ADP to ATP, may be preferably used in an amount of from 1 U/ml to 100 U/ml.

As the phosphate donor, acetyl phosphate is used. Acetyl phosphate acid may be used in the form of ammonium, potassium/lithium or sodium salts. From the viewpoint of availability, disodium acetyl phosphate may be preferably used. It is preferable to use acetyl phosphate in an amount of from 1/10 to 100 equivalents, still preferably from 1 to 50 equivalents, to the ATP concentration. It may be added by an arbitrary method. Namely, it may be added either at once at the initiation of the reaction or in portions.

A determination method employed in the present invention as well as methods for determining the activities of the employed enzymes will be described hereinafter.

(1) Method for Determining ATP Sulfurylase Activity

A reaction solution of the composition as specified below is maintained at 30° C. and an appropriate amount of an enzyme sample solution is added to thereby initiate the reaction. After 10 minutes, the reaction is terminated by adding 0.05 ml of 3N sulfuric acid. After the completion of the reaction, the concentration of phosphoric acid is determined by using a reagent for the determination of inorganic phosphoric acid (Phospha C-Test Wako, a product of Wako Pure Chemical Industries, Inc.).

The amount of ATP sulfurylase capable of forming 2 $\mu$mol of phosphoric acid, i.e., 1 $\mu$mol of pyrophosphoric acid per minute is referred to as 1 U (unit).

| Composition of reaction solution (total amount: 0.5 ml) | |
|---|---|
| Tris-HCl buffer solution (pH 8) | 100 mM |
| magnesium chloride | 10 mM |
| sodium molybdate | 10 mM |
| ATP | 10 mM |
| pyrophosphatase | 0.4 U/ml |
| sample (ATP sulfurylase solution) | q.s. |
| (Reaction formulae) | |

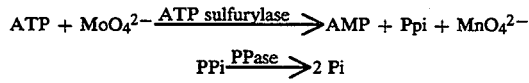

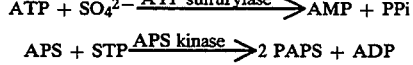

(2) Method for Determining APS Kinase Activity

A reaction solution of the composition as specified below is maintained at 30° C. and an appropriate amount of an enzyme sample solution is added to thereby initiate the reaction. After 10 minutes, the reaction is terminated by heating the mixture in a boiling water bath for 1 minute. After the completion of the reaction, the amount of the PAPS thus formed is determined by HPLC.

The amount of APS kinase capable of forming 1 $\mu$mol of PAPS per minute is referred to as 1 U (unit).

| Composition of reaction solution (total amount: 0.5 ml) | |
|---|---|
| Tris-HCl buffer solution (pH 8) | 100 mM |
| magnesium sulfate | 10 mM |
| ATP | 1 mM |
| ATP sulfurylase | 0.5 U/ml |
| sample (APS kinase solution) | q.s. |
| (Reaction formulae) | |

ATP + SO$_4^{2-}$ $\xrightarrow{\text{ATP sulfurylase}}$ AMP + PPi

APS + STP $\xrightarrow{\text{APS kinase}}$ 2 PAPS + ADP

(3) Method for Determining Pyrophosphatase Activity

A reaction solution of the composition as specified below is maintained at 30° C. and an appropriate amount of an enzyme sample solution is added to thereby initiate the reaction. After 10 minutes, the reaction is terminated by adding 0.05 ml of 3N sulfuric acid. After the completion of the reaction, the concentration of phosphoric acid is determined by using a reagent for the determination of inorganic phosphoric acid (Phospha C-Test Wako, a product of Wako Pure Chemical Industries, Inc.). The amount of pyrophosphatase capable of forming 2 $\mu$mol of phosphoric acid, i.e., 1 $\mu$mol of pyrophosphoric acid per minute is referred to as 1 U (unit).

| Composition of reaction solution (total amount: 0.5 ml) | |
|---|---|
| Tris-HCl buffer solution (pH 8) | 100 mM |
| magnesium chloride | 5 mM |
| sodium pyrophosphate | 5 mM |
| sample (pyrophosphatase) | q.s. |
| (Reaction formula) | |

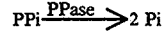

(4) Method for Determining Acetate Kinase (AK) Activity

A reaction solution of the composition as specified below is maintained at 30° C. and pre-heated for 3 minutes.

| Composition of reaction solution (total amount: 2.4 ml) | |
|---|---|
| imidazole hydrochloride buffer solution (pH 7.2) | 70 mM |
| magnesium chloride | 250 mM |
| potassium chloride | 94 mM |
| ATP | 12.5 mM |
| phosphoenolpyruvic acid (PEP) | 4.2 mM |
| NADH | 3.3 mM |
| pyruvate kinase (PK) | 240 U |
| lactate dehydrogenase (LDH) | 330 U |

To this reaction solution, 0.6 ml of a 2M sodium acetate solution is added.

A sample (acetate kinase) is dissolved in a 50 mM phosphate buffer in such a manner as to give a concentration of 5 to 10 U/ml. 0.01 ml of the obtained sample solution is then added to the above-mentioned reaction solution.

The UV absorbance at 340 nm is measured every other minute and the slope of the linear part is determined.

$$\text{Activity (U/ml)} = \frac{(\Delta Abs\ 340) \times (3.00 + 0.01)}{6.22 \times 0.01} \times d.f.$$

$$\text{Specific activity (U/mg protein)} = \frac{\text{activity (U/ml)}}{\text{activity conc. (mg/ml)}}$$

d.f.: coefficient of dilution.
6.22: molecular absorption coefficient of NADH (cm$^2$/$\mu$mol).

Enzyme conc.: determined by Bradford's method.

The amount of acetate kinase capable of forming 1 $\mu$mol of ADP per minute is referred to as 1 unit.

(5) Method for Determining PAPS by HPLC

PAPS is determined with the use of a $\mu$bondapak C18 column (a product of Waters Co.).

| Composition of mobile phase: | |
|---|---|
| tetrabutylammonium perchlorate | 3 mm |
| monopotassium phosphate | 30 mm |

-continued

| Composition of mobile phase: | |
|---|---|
| methanol | 25 vol. % |
| water | 75 vol. %. |

The flow rate is 0.6 ml/min. and the product is detected by measuring the UV absorption (λ=254 nm).

To further illustrate the present invention in greater detail, the following Examples will be given.

Reference Example 1

A medium containing 1% by weight of glucose, 1% by weight of yeast extract, 0.1% by weight of phosphoric acid and a small amount of minerals was sterilized and adjusted to pH 6.5. Then *Bacillus thermophilus* (NCA 1503 strain) was inoculated thereto and incubated.

After incubating at 60° C. for 3 hours, it was confirmed that the glucose in the medium had been consumed and then the cells were collected by centrifuging.

Reference Example 2

Wet cells obtained by the same method as the one described in the above Reference Example 1 were disrupted by the freezing and thawing method. Next, nucleic acids were removed by using a polyacrylamide coagulant. The precipitate thus formed was removed by centrifuging and thus a crude enzyme solution was obtained.

The crude enzyme solution was applied onto a DEAE-Sepharose column which had been previously equilibrated with a 50 mM Tris-HCl buffer solution (pH 8.0). The ATP sulfurylase thus adsorbed was thoroughly washed with the same buffer solution and then developed by linear gradient elution with 0 to 500 mM sodium chloride with the use of the same buffer solution. The active fraction was collected and ammonium sulfate was added in such a manner as to give a concentration of 1M.

This active fraction was applied onto a Phenyl Sepharose column equilibrated with a 50 mM Tris-HCl buffer solution (pH 8.0) containing 1M of ammonium sulfate. After thoroughly washing with the same buffer solution, elution was made with the use of a 50 mM Tris-HCl buffer solution (pH 8.0).

The active fraction thus obtained was collected, concentrated, dialyzed and then applied onto a Martex Gel Blue A column equilibrated with a 50 mM Tris-HCl buffer solution (pH 8.0). After thoroughly washing with the same buffer solution, elution was made with the use of the same buffer solution containing 1M of potassium chloride.

The active fraction was collected, concentrated and then subjected to polyacrylamide gel electrophoresis. As a result, a single band was obtained.

The specific activity of the enzyme preparation was 11.1 U/mg.

Reference Example 3

Wet cells obtained by the same method as the one described in the above Reference Example 1 were disrupted by the freezing and thawing method. Next, nucleic acids were removed by using a polyacrylamide coagulant. The precipitate thus formed was removed by centrifuging and thus a crude enzyme solution was obtained.

The crude enzyme solution was applied onto a DEAE-Sepharose column which had been previously equilibrated with a 50 mM Tris-HCl buffer solution (pH 8.0). The APS kinase thus adsorbed was thoroughly washed with the same buffer solution and then developed by linear gradient elution with 0 to 500 him sodium chloride with the use of the same buffer solution. The active fraction was collected and ammonium sulfate was added in such a manner as to achieve 70% saturation. After centrifuging, the precipitate was dissolved in the same buffer solution and dialyzed.

After applying onto a Martex Gel Blue A column equilibrated with the same buffer solution, and after thoroughly washing with the same buffer solution, a phosphate buffer solution (pH 7.2) containing 1.5M of potassium chloride was passed through the column.

To the active fraction thus obtained, ammonium sulfate was added in such a manner as to give a concentration of 800 mM. Then the obtained mixture was applied onto a Phenyl Cellulofine column equilibrated with a 50 mM Tris-HCl buffer solution (pH 8.0) containing 800 mM of ammonium sulfate. After thoroughly washing with the same buffer solution, a 50 mM Tris-HCl buffer solution (pH 8.0) was passed through the column.

The active fraction was collected, concentrated and then subjected to polyacrylamide gel electrophoresis. As a result, a single band was obtained.

The specific activity of the enzyme preparation was 1.1 U/mg.

Now, Examples will be given in order to illustrate the first embodiment of the present invention.

Example 1

In a thermostated reactor of 150 L in capacity, 100 L of an aqueous solution containing 5 mM of Tris-HCl buffer solution, 100 mM of ATP, 100 mM of magnesium sulfate and 100 mM of sodium sulfate was prepared. After adjusting to pH 8 with sodium hydroxide, the aqueous solution was maintained at 30° C. Then 25,000 U of heat-stable ATP sulfurylase originating from *Bacillus stearothermophilus* NCA-1503 (ATCC 29609), 50,000 U of APS kinase of the same origin and 50,000 U of pyrophosphatase originating from yeast (Boehringer.Mannheim & Yamanouchi) were added thereto and the reaction was initiated. After reacting for 24 hours, the enzymes were separated from the residual matter by using an ultrafiltration membrane. The enzyme solution thus obtained was stored at 4° C. until subsequent use. The results of the analysis of the reaction mixture by HPLC indicated that 4.46 mol of PAPS was formed and the conversion ratio based on ATP was 44.6 mol%. The reaction mixture free from the enzyme solution was passed over 500 L of a DEAE-Sepharose column and developed by linear gradient elution with 0 to 400 mM of sodium chloride solution to thereby separate PAPS from the reaction mixture. The PAPS aqueous solution was further concentrated and desalted with the use of a reverse osmosis membrane NTR-7250 (a product of Unitika Ltd.) and then freeze dried. Thus 2,522 g of a white powder was obtained (isolation yield: 95% by weight). After analyzing by NMR and ESCA, it was found out that the product comprised PAPS.4Na of a purity of 99 mol%.

Example 2

Two necks of a three-necked glass enzyme reactor (capacity: 150 ml) were provided each with a tube and connected to a flat membrane ultrafiltration device (a product of Millipore Co.). Then 250 ml of a 5 mM Tris-HCl buffer solution (pH 8.0) was added thereto and circulated at a flow rate of 1 L/hr. The whole reactor was maintained at 40° C. From another inlet of this reactor, 250 U of ATP sulfurylase and 500 U of APS kinase, each originating from *Thermus flavus* (ATCC 33923), and 500 U of pyrophosphatase originating from *Bacillus stearothermophilus* were added. Then this neck was provided with a tube and a mixture of 50 mM of ATP, 50 mM of magnesium sulfate and 50 mM of sodium sulfate dissolved in the same buffer solution as the circulating one was added at a flow rate of 50 ml/hr. Some portion of the solution passing through the above-mentioned ultrafiltration membrane was continuously collected at a rate of 50 ml/hr and stored at 2° C. This reaction was performed for 62 hours and thus 3.1 L of a PAPS aqueous solution was obtained. The conversion ratio of PAPS based on ATP was 39 mol%. Then PAPS was isolated and purified in the same manner as employed in the above Example 1. Thus 34.9 g of PAPS.4Na of a purity of 99 mol% was obtained (isolation yield: 97% by weight).

Example 3

By using the same reactor as the one employed in the above Example 2, the procedure of Example 2 was repeated except that ATP sulfurylase and APS kinase, each originating from *Bacillus Stearothermophilus* (NCA-1503; ATCC 29609), were used. The reaction temperature was maintained at 30° C. After reacting for 108 hours, 5.4 L of a PAPS aqueous solution was obtained. The conversion ratio of PAPS based on ATP was 42 mol%. Then PAPS was isolated and purified in the same manner as employed in the above Example 1. Thus 64.1 g of PAPS.4Na of a purity of 99% was obtained (isolation yield: 95% by weight).

Example 4

100 U of ATP sulfurylase originating from *Thermus flavus* (ATCC 33923) was kneaded with 10 ml of 10% by weight gelatin and then strained with a wire net of a fine mesh. The particles thus obtained were immersed in 5% by weight of glutaraldehyde at 4° C. for 1 hour and then thoroughly washed with water to thereby give an immobilized enzyme. Further, 200 U of APS kinase of the same origin and 200 U of pyrophosphatase of the same origin were each formulated into an immobilized enzyme in the same manner. Each of these immobilized enzymes was packed into a column of 3 cm in diameter and 6 cm in height. Then, 200 ml of a 50 mM Tris-HCl buffer solution (pH 8.0) containing 100 mM of ATP, 100 mM of magnesium sulfate and 100 mM of sodium sulfate was passed through the column at a flow rate of 0.5 ml/min. The column was maintained at 40° C. When the solution passed through the column was examined, the reaction ratio of PAPS based on ATP was 46 mol%. After passing the solution for 7 hours, PAPS was isolated from the reaction-mixture and purified by the same method as the one described in the above Example 1. As a result, 5.31 g of PAPS.4Na of a purity of 99 mol% was obtained (isolation yield: 97% by weight).

Comparative Example 1

By using the same reactor as the one employed in the above Example 2, the procedure of Example 3 was repeated except that ATP sulfurylase and APS kinase, each originating from a yeast *Saccharomyces cerevisiae* (ATCC 7752), were used. After reacting for 60 hours, 3.0 L of a PAPS aqueous solution was obtained.

The conversion ratio of PAPS based on ATP was 2.2 mol%. Then PAPS was isolated and purified in the same manner as employed in the above Example 1. Thus 1.91 g of PAPS.4Na of a purity of 99 mol% was obtained (isolation yield: 97% by weight).

Next, Examples will be given in order to illustrate the second embodiment of the present invention.

Example 5

In a 200 ml flask, a reaction solution of the composition as specified below was prepared and maintained at 30° C. The employed four enzymes were all heat-stable and originating from *Bacillus stearothermophilus* (NCA-1503, ATCC 29609). The total amount of the reaction solution was 100 ml.

| | |
|---|---|
| Tris-HCl buffer solution (pH 8.0) | 25 mM |
| magnesium sulfate | 40 mM |
| ATP | 20 mM |
| Acetyl Phosphate (AcOP) | 20 mM |
| acetate kinase (AK) | 500 U |
| PPase | 200 U |
| ATP sulfurylase | 10 U |
| APS kinase | 20 U |

As the AK, a product of Unitika Ltd. was employed, while a product of Boehringer, Mannheim & Yamanouchi was employed as the PPase.

The ATP sulfurylase used herein was obtained by purifying an enzyme originating from *Bacillus stearothermophilus*, which had been incubated by the same method as described in the above Reference Example 1, by the same method as described in the above reference example 2.

The APS kinase used herein was obtained by purifying an enzyme originating from *Bacillus stearothermophilus*, which had been incubated by the same method as described in the above Reference Example 1, by the same method as described in the above Reference Example 3.

After initiation of the reaction, an aqueous solution of acetyl phosphate in an amount corresponding to 10 mM was added at intervals of 4 hours. After reacting for 24 hours, the reaction mixture was analyzed by HPLC. As a result, 1.34 mmol of PAPS was formed and the conversion ratio based on ATP was 68 mol%.

The enzyme-free reaction mixture was applied to a 1 L DEAE-Sepharose column and developed by linear gradient elution with 0 to 400 mM of sodium chloride solution to thereby separate PAPS from the reaction mixture. The PAPS aqueous solution was further concentrated and desalted with the use of a reverse osmosis membrane NTR-7250 (a product of Unitika Ltd.) and then freeze dried. Thus 0.76 g of a white powder was obtained (purification yield: 95% by weight). After analyzing by NMR and ESCA, it was found out that the product comprised PAPS.4Na of a purity of 99 mol%.

Example 6

Two necks of a three-necked glass enzyme reactor (capacity: 150 ml) were provided each with a tube and connected to a flat membrane ultrafiltration device (a product of Millipore Co.). Then 250 ml of a 5 mM Tris-HCl buffer solution (pH 8.0) was added thereto and circulated at a flow rate of 1 L/hr. The whole reactor was maintained at 40° C. From another inlet of this reactor, 20 U of ATP sulfurylase and 40 U of APS kinase, both originating from *Bacillus stearothermo*-

*philus*, 500 U of acetate kinase and 100 U of PPase were added.

As the AK, a product of Unitika Ltd. was used while a product of Boehringer, Mannheim & Yamanouchi was employed as the PPase.

The ATP sulfurylase used herein was obtained by purifying an enzyme originating from *Bacillus stearothermophilus*, which had been incubated by the same method as the one described in the above Reference Example 1, by the same method as the one described in the above reference example 2.

The APS kinase used herein was obtained by purifying an enzyme originating from *Bacillus stearothermophilus*, which had been incubated by the same method as described in the above Reference Example 1, by the same method as described in the above Reference Example 3.

Then this neck was provided with a tube and a mixture of 50 mM of ATP and 50 mM of magnesium sulfate dissolved in the same buffer solution as the circulating buffer solution was added at a flow rate of 50 ml/hr. Some portion of the solution passing through the above-mentioned ultrafiltration membrane was continuously collected at a rate of 50 ml/hr and stored at 2° C. This reaction was performed for 40 hours and thus 2.0 L of a PAPS aqueous solution was obtained. The conversion ratio of PAPS based on ATP was 65 mol%. Then PAPS was isolated and purified in the same manner as employed in the above Example 1. Thus 36.7 g of PAPS.4Na of a purity of 99 mol% was obtained (isolation yield: 95% by weight).

Comparative Example 2

By using the same reactor as the one employed in the above Example 5, the procedure of Example 5 was repeated except that no acetate kinase was added. After reacting for 24 hours, the conversion ratio of PAPS based on ATP was 33 mol%. Then PAPS was isolated and purified in the same manner as employed in the above Example 5. Thus 0.36 g of PAPS.4Na of a purity of 99 mol% was obtained (isolation yield: 94% by weight).

Comparative Example 3

By using the same reactor as the one employed in the above Example 6, the procedure of Example 6 was repeated except that no acetate kinase was added. After reacting for 40 hours, 2.0 L of a PAPS aqueous solution was obtained and the conversion ratio of PAPS based on ATP was 29 mol%. Then PAPS was isolated and purified in the same manner as employed in the above Example 5. Thus 15.9 g of PAPS.4Na of a purity of 99 mol% was obtained (isolation yield: 92% by weight).

Comparative Example 4

By using the same reactor as the one employed in the above Example 6, the procedure of Example 6 was repeated except that ATP sulfurylase and APS kinase, each originating from a yeast *Saccharomyces cerevisiae* (ATCC 7752), were used. After reacting for 60 hours, 3.0 L of a PAPS aqueous solution was obtained.

The conversion ratio of PAPS based on ATP was 2.2 mol%. Then PAPS was isolated and purified in the same manner as employed in the above Example 1. Thus 1.91 g of PAPS.4Na of a purity of 99% by weight was obtained (isolation yield: 97% by weight).

Example 7

By using the same reactor as the one employed in the above Example 5, the procedure of Example 5 was repeated except that the reaction temperature was adjusted to 40° C. After reacting for 8 hours, the conversion ratio of PAPS based on ATP was 70 mol%. Then PAPS was isolated and purified in the same manner as employed in the above Example 5. Thus 0.77 g of PAPS.4Na of a purity of 99 mol% was obtained (isolation yield: 94% by weight).

Example 8

By using the same reactor as the one employed in the above Example 5, the procedure of Example 5 was repeated except that an HEPES buffer solution (pH 7.0) was used as the buffer solution. After reacting for 24 hours, the conversion ratio of PAPS based on ATP was 66 mol%. Then PAPS was isolated and purified in the same manner as the one employed in the above Example 5. Thus 0.72 g of PAPS.4Na of a purity of 99 mol% was obtained (isolation yield: 95% by weight).

The method of the present invention makes it possible to remarkably increase the production of PAPS and to easily isolate and purify the product, compared with conventional methods for producing PAPS. Therefore, the present invention provides a highly advantageous method for producing PAPS on an industrial scale.

While the invention has been described in detail and with reference to specific examples thereof, it will be apparent to one skilled in the art that various changes and modifications can be made therein without departing from the spirit and scope thereof.

What is claimed is:

1. A method for producing 3'-phosphoadenosine 5'-phosphosulfate which comprises (1) reacting adenosine 5'-triphosphate with a sulfate donor in the presence of heat-stable adenosine 5'-triphosphate sulfurylase obtained from *Bacillus stearothermophilus* (ATCC 29609) to produce adenosine 5'-phosphosulfate, and (2) reacting said adenosine 5'-phosphosulfate with adenosine 5'-triphosphate in the presence of heat-stable adenosine 5'-phosphosulfate kinase obtained from *Bacillus stearothermophilus* (ATCC 29609).

2. The method of claim 1, wherein adenosine 5'-diphosphate produced in said step (2) is converted into adenosine 5'-triphosphate in the presence of a phosphate donor and an enzyme that converts adenosine 5'-diphosphate into adenosine 5'-triphosphate.

3. A method as claimed in claim 1 or 2, wherein said sulfate donor is a member selected from the group consisting of magnesium sulfate, sodium sulfate, potassium sulfate, lithium sulfate and beryllium sulfate.

4. A method as claimed in claim 2, wherein said phosphate donor is acetyl phosphate.

5. A method as claimed in claim 1 or 2, wherein the reaction is performed at a pH value ranging from 5 to 11.

6. A method as claimed in claim 1 or 2, wherein the reaction is performed at a pH value ranging from 6 to 9.

7. A method as claimed in claim 1 or 2, wherein the reaction is performed at a temperature ranging from 20° to 70° C.

8. A method as claimed in claim 1 or 2, wherein the reaction is performed at a temperature ranging from 25° to 45° C.

9. A method as claimed in claim 1 or 2, wherein the reaction is performed at an adenosine 5'-triphosphate concentration of 200 mM or lower.

10. A method as claimed in claim 1 or 2, wherein the reaction is performed at an adenosine 5'-triphosphate concentration of 100 mM or lower.

11. A method as claimed in claim 1, wherein said heat-stable adenosine 5'-triphosphate sulfurylase and heat-stable adenosine 5'-phosphosulfate kinase have an optimal temperature of 40° C. or higher for the activity thereof.

12. A method as claimed in claim 2, wherein said enzyme that converts adenosine 5'-diphosphate into adenosine 5'-triphosphate is acetate kinase.

* * * * *